(12) United States Patent
Muñoz Muñoz

(10) Patent No.: US 10,334,806 B2
(45) Date of Patent: Jul. 2, 2019

(54) LETTUCE VARIETY NUN 06773 LTL

(71) Applicant: Nunhems B.V., AB Nunhem (NL)

(72) Inventor: Juan Francisco Muñoz Muñoz, Nunhem (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 15/636,768

(22) Filed: Jun. 29, 2017

(65) Prior Publication Data

US 2017/0359993 A1   Dec. 21, 2017

(51) Int. Cl.
  *A01H 5/12*   (2018.01)
  *A01H 6/14*   (2018.01)

(52) U.S. Cl.
  CPC ............. *A01H 6/1472* (2018.05); *A01H 5/12* (2013.01)

(58) Field of Classification Search
  None
  See application file for complete search history.

(56) References Cited

U.S. PATENT DOCUMENTS

| | | | | |
|---|---|---|---|---|
| 7,321,078 B1 * | 1/2008 | Knerr | ......................... | A01H 5/12 435/410 |
| 7,371,930 B1 * | 5/2008 | Knerr | ......................... | A01H 5/12 435/410 |
| 2008/0222949 A1 | 9/2008 | Bissonnette et al. | | |

FOREIGN PATENT DOCUMENTS

| | | |
|---|---|---|
| EP | 1197137 A1 | 4/2002 |
| WO | 2013182646 A1 | 12/2013 |

OTHER PUBLICATIONS

Guidelines for the conduct of tests for distinctness, uniformity and stability, UPOV (International Union for the Protection of New Varieties and Plants); Apr. 5, 2006.

Objective description of Variety—Lettuce (*Lactuca sativa* L.), U.S. Department of Agriculture, Agricultural Marketing Service, Science and Technology, Plant Variety Protection Office, Beltsville, MD 20705; Jul. 1, 2009.

Teng, Whei-Lan, et al., Rapid Regeneration of Lettuce from Suspension Culture, HortScience, 1992, pp. 1030-1032, vol. 27, No. 9.

Teng, Whei-Lan, et al., Regenerating Lettuce from Suspension Culture in a 2-Liter Bioreactor, HortScience, 1993, pp. 669-671, vol. 28, No. 6.

Zhang, Xinrun, et al., Genotypic effects on tissue culture response of lettuce cotyledons, Journal of Genetics and Breeding, 1992, pp. 287-290, vol. 46, No. 3.

Gonai, Takeru, et al., Abscisic acid in the thermoinhibition of lettuce seed germination and enhancement of its catabolism by gibberellin, Journal of Experimental Botany, Jan. 2004, pp. 111-118, vol. 55, No. 394.

Jackson, Louise, et al, Iceberg Lettuce Production in California, University of California, Division of Agriculture and Natural Resources, Publication 7215, ISBN 978-1-60107-007-4 (publication date not available).

Jackson, Louise, et al, Leaf Lettuce Production in California, University of California, Division of Agriculture and Natural Resources, Publication 7216, ISBN 978-1-60107-008-1 (publication date not available).

Vos, Pieter, et al., AFLP: a new technique for DNA fingerprinting, Nucleic Acid Research, 1995, pp. 4407-4414, vol. 23, No. 21.

Brotman, Y., et al., Resistance gene homologues in melon are linked to genetic loci conferring disease and pest resistance, Theor Appl Genet, 2002, pp. 1055-1063, vol. 104.

Dziechciarková, M., et al, Characterization of *Lactuca* spp. Germplasm by protein and molecular markers—a review, Plant Soil Environ., 2004, pp. 47-58, vol. 50, No. 2.

Clewer, Alan G. and Scarisbrick, David H., Practical Statistics and Experimental Design for Plant and Crop Science, John Wiley & Sons, Ltd., 2001.

* cited by examiner

*Primary Examiner* — Ashley K Buran
(74) *Attorney, Agent, or Firm* — Arent Fox LLP

(57) ABSTRACT

The invention relates to a new variety of lettuce designated NUN 06773 LTL as well as seeds and plants and heads or leaves thereof.

21 Claims, No Drawings

LETTUCE VARIETY NUN 06773 LTL

FIELD OF THE INVENTION

The present invention relates to the field of plant breeding and, more specifically, to the development of lettuce variety NUN 06773 LTL (also designated as NUN 06773 or 06773 LTL or NUN 6773 or 6773 LTL or "Themes"). The invention further relates to vegetative reproductions of NUN 06773 LTL, methods for in vitro tissue culture of NUN 06773 LTL, an explant and also to phenotypic variants of NUN 06773 LTL.

The goal of vegetable breeding is to combine various desirable traits in a single variety. Such desirable traits may include greater yield, resistance to diseases, insects or other pests, tolerance to heat and drought, better agronomic quality, higher nutritional value, enhanced growth rate and improved shelf life.

The development of commercial lettuce cultivars or varieties requires the crossing of lettuce plants, and the evaluation of the crosses. Pedigree breeding and recurrent selection are examples of breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the inbred lines or hybrids from these crosses are evaluated to determine which have commercial potential.

All cultivated forms of lettuce belong to the highly polymorphic species *Lactuca sativa* that is grown for its edible head and leaves. *Lactuca sativa* is in the *Asteraceae* (Compositae) family Lettuce is related to chicory, sunflower, aster, dandelion, artichoke and *chrysanthemum*. *L. sativa* is one of about 300 species in the genus *Lactuca*. There are many types of lettuce, and new types are constantly in development. Types of lettuce include Cutting/Leaf, Iceberg/Crisphead, Cos or Romaine, Batavia, Salinas Group, Latin, Butterhead, Great Lakes Group, Eastern (Ithaca) Group, Bibb, Vanguard Group, multileaf or Stem lettuce.

Fresh lettuce is available in the United States year-round although the greatest supply is from May through October. For planting purposes, the lettuce season is typically divided into three categories, early, mid and late, with the coastal areas planting from January to August, and the desert regions planting from August to December. Lettuce is consumed nearly exclusively as fresh, raw product and occasionally as a cooked vegetable.

Lifestyles change and the demand from restaurants and catering firms for colorful and interesting garnish for sandwiches and ready-to-use processed salads continue to rise. As a result, there is a demand for breeding companies to develop new varieties with specific shapes of leaves, specific average size of leaves, glossiness, prominent color and a wide variety of texture, as well as good yield.

SUMMARY OF THE INVENTION

In an aspect of the invention, a seed of lettuce variety NUN 06773 LTL is provided, wherein a representative sample of said seed has been deposited under Accession Number NCIMB 42769. The seed of the lettuce variety of the invention may be provided as an essentially homogeneous population of lettuce seed. Therefore, seed of the invention may be defined as forming at least about 97% of the total seed, including at least about 98%, 99% or more of the seed of said variety. The population of lettuce seed may be particularly defined as being essentially free from other seed. The seed population may be grown to provide an essentially homogeneous population of lettuce plants according to the invention. Also encompassed are a plant grown from a seed of lettuce variety NUN 06773 LTL and a plant part of said variety.

In another aspect the invention provides a variety of *Lactuca sativa* called NUN 06773 LTL. The invention also provides a seed or a plurality of seeds of said new variety, plants produced from growing the seed of the variety NUN 06773 LTL, and progeny of any of these. Especially, a plant or a progeny retaining all, or all but one, two or three, of the "distinguishing characteristics", or all, or all but one, two or three, of the "morphological and physiological characteristics" of said variety, is encompassed herein, as well as methods for producing this plant or progeny.

In one aspect, such a plant or such a progeny has all the physiological and morphological characteristics of variety NUN 06773 LTL when grown under the same environmental conditions. In another aspect such a plant or progeny plant has all the physiological and morphological characteristics as listed in Table 1 and/or 2 and/or 3 for NUN 06773 LTL when measured under the same environmental conditions (i.e. evaluated at significance levels of 1%, 5% or 10% significance, which can also be expressed as a p-value).

In another aspect a plant of NUN 06773 LTL or a progeny plant comprises 4, 5, or 6 of the distinguishing characteristics from the group: 1) average core height (see in Table 1 core height from base of head to apex); 2) average core diameter (see in Table 1 diameter at base of head); 3) degree of mature leaf blistering (see Table 1 Blistering=medium); 4) degree of undulation of the apical margin (see Table 1 Margin: undulation of the apical margin=absent/slight); 5) core height range (see Table 1 core height from base of head to apex—range); and 6) mature leaf green color (see Table 1 Green color: medium green). NUN 06773 LTL is a Little Gem lettuce type. Little Gem lettuce is even shorter than Mini Romaine lettuce types.

Further, a lettuce head and/or a lettuce leaf produced on a plant grown from these seeds is provided.

In yet another embodiment of the invention, a plant having one, two or three physiological and/or morphological characteristics which are different from those of the lettuce variety of the invention and which otherwise has all the physiological and morphological characteristics of NUN 06773 LTL as listed in Table 1 and/or 2 and/or 3 is encompassed herein, wherein a representative sample of seed of variety NUN 06773 LTL has been deposited under Accession Number NCIMB 42769.

Further, a vegetatively propagated plant of variety NUN 06773 LTL, or a part thereof, is provided having all, or all but one, two or three, of the morphological and physiological characteristics NUN 06773 LTL when grown under the same environmental conditions.

Also a plant part obtained from variety NUN 06773 LTL is provided, wherein said plant part is selected from the group consisting of: a fruit, a part of a fruit, a leaf, a part of a leaf, a head, a part of a head, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, a cotyledon, a rootstock, a pistil, an anther, and a flower or a part thereof. Heads and leaves are particularly important plant parts. In yet another aspect, a seed of NUN 06773 LTL is provided (i.e. a seed which when grown grows into variety NUN 06773 LTL). In still another aspect, a seed produced on a plant of NUN 06773 LTL is provided (i.e. after pollination of the flower of NUN 06773 LTL).

DEFINITIONS

All patent and non-patent literatures cited herein are incorporated by reference in their entireties.

"Lettuce" refers herein to plants of the species *Lactuca sativa* L. The most commonly eaten parts of a lettuce plant are the head or a leaf. The head comprises a core and leaves, which may be divided in inner and outer leaves.

"Cultivated lettuce" refers to plants of *Lactuca sativa* i.e. varieties, breeding lines or cultivars of the species *L. sativa* cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of *Lactuca sativa*, comprising, for example *L. virosa* or *L. serriola*, and other related species.

The terms "NUN 06773 LTL", "Themes" "lettuce NUN 06773 LTL", "NUN 06773", "06773 LTL" "NUN 6773", "6773 LTL" or "variety NUN 06773 LTL" are used interchangeably herein and refer to a lettuce plant of variety NUN 06773 LTL, representative seed of which having been deposited under Accession Number NCIMB 42769.

A "seed of NUN 06773 LTL" refers to a seed of NUN 06773 LTL, which can be grown into a plant of NUN 06773 LTL wherein a representative sample of said seed has been deposited under Accession Number NCIMB 42769. When said seed is planted, it grows into a plant of NUN 06773 LTL.

An "embryo of NUN 06773 LTL" refers to an embryo as present in a seed of NUN 06773 LTL, wherein a representative sample of said seed has been deposited under Accession Number NCIMB 42769.

A "seed grown on NUN 06773 LTL" or a "seed produced on NUN 06773 LTL" refers to a seed grown on a mature plant of NUN 06773 LTL or a seed inside a fruit of NUN 06773 LTL. The "seed grown on NUN 06773 LTL" contains tissues and DNA of the maternal parent, NUN 06773 LTL. The "seed grown on NUN 06773 LTL" contains an F1 embryo (usually a first generation selfing). When said seed is planted, it grows into a first generation progeny plant of NUN 06773 LTL.

"USDA descriptors" are the plant variety descriptors described for lettuce in the "Objective description of Variety—Lettuce (*Lactuca sativa* L.)", as published by U.S. Department of Agriculture, Agricultural Marketing Service, Science and Technology, Plant Variety Protection Office, Beltsville, Md. 20705 and which can be downloaded from the world wide web at ams.usda.gov/ under sites/default/files/media/01-Lettuce%20ST-470-01%202015.pdf.

"UPOV descriptors" are the plant variety descriptors described for lettuce in the "Guidelines for the Conduct of Tests for Distinctness, Uniformity and Stability," TG/013/10 (Geneva 2006, last updated Mar. 20, 2013), as published by UPOV (International Union for the Protection of New Varieties and Plants) and which can be downloaded from the world wide web at upov.int/ under edocs/tgdocs/en/tg013.pdf and is herein incorporated by reference in its entirety. Likewise, "UPOV methods" to determine specific parameters for the characterization of lettuce are described at upov.int.

"RHS" refers to the Royal Horticultural Society of England which publishes an official botanical color chart quantitatively identifying colors according to a defined numbering system, The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE; sold by, e.g., TORSO-VERLAG, Obere Grüben 8 • D-97877 Wertheim, Article-No.: Art62-00008 EAN-Nr.: 4250193402112).

As used herein and except as otherwise indicated, the term "plant" includes the whole plant or any part thereof, preferably having the same genetic makeup as the plant from which it is obtained, such as a plant organ (e.g. harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, or parts of a plant (e.g. harvested tissues or organs), such as a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, seed coat or another maternal tissue which is part of a seed grown on a variety of the invention, hypocotyl, cotyledon, a graft, a rootstock, a pistil, an anther, and a flower or parts of any of these and the like. Also any developmental stage is included, such as seedlings, cuttings prior or after rooting, mature plants or leaves. Alternatively, a plant part may also include a plant seed which comprises one or two sets of chromosomes derived from the parent plant, e.g. from NUN 06773 LTL. An F1 progeny produced from self-pollination of NUN 06773 LTL will thus comprise two sets of chromosomes derived from NUN 06773 LTL, while an F1 progeny derived from cross-fertilization of NUN 06773 LTL will comprise only one set of chromosomes from NUN 06773 LTL and the other set of chromosomes from the other parent.

"Cotyledon" refers to one of the first leaves of the embryo of a seed plant; typically one or more in monocotyledons, two in dicotyledons and two or more in gymnosperms.

"Head" as used herein refers to lettuce heads, i.e., the plant without the root system, for example substantially all harvested leaves. Encompassed are immature leaves (e.g. "baby leaf") and mature leaves.

The "base" of a plant is the part of a lettuce plant where the leaves are attached to the root system of the plant.

"Core height" refers to the average height of the core from its base to its apex.

"Head weight" refers to the average weight of saleable lettuce head, cut and trimmed to market specifications.

"Head diameter" refers to the average diameter of the cut and trimmed head, sliced vertically, and measured at the widest point perpendicular to the stem.

"Head height" refers to the mean height of the cut and trimmed head, sliced vertically, and measured from the base of the cut stem to the leaf tip.

"Core Ratio of Head Diameter/Core diameter" refers to the average head diameter/core diameter ratio. It is calculated by dividing the average head diameter by the average core diameter. This is an indication of the head shape.

"Harvested plant material" refers herein to plant parts (e.g., leaves or heads detached from the whole plant) which have been collected for further storage and/or further use.

"Harvested seeds" refers to seeds harvested from a line or variety, e.g., produced after self-fertilization or cross-fertilization and collected.

"REFERENCE VARIETY" refers herein to variety 3SX4901, a commercial variety from company 3 STAR LETTUCE LLC., which has been planted in a trial together with NUN 06773 LTL. USDA descriptors of NUN 06773 LTL were compared to the USDA descriptors of 3SX4901.

"Yield" means the total weight of all lettuce heads or leaves harvested per hectare of a particular line or variety. It is understood that "yield" expressed as weight of all lettuce heads or leaves harvested per hectare can be obtained by multiplying the number of plants per hectare times the "yield per plant".

"Marketable yield" means the total weight of all marketable lettuce heads or leaves harvested per hectare of a particular line or variety, i.e. lettuce heads or leaves suitable for being sold for fresh consumption, having good color, glossiness size and texture and no or very low levels of deficiencies.

A plant having "all the physiological and morphological characteristics" of a referred-to-plant means a plant having or showing the physiological and morphological characteristics of the referred-to-plant when grown under the same environmental conditions, preferably in the same experiment next to each other. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 and/or 2 and/or 3 or "all or all but one, two or three of the physiological and morphological characteristics" of Table 1 and/or 2 and/or 3.

NUN 06773 LTL has 6 distinguishing characteristics when compared to REFERENCE VARIETY. For NUN 06773 LTL these distinguishing characteristics are 1) average core height; 2) average core diameter; 3) type of mature leaf blistering; 4) type of undulation of the apical margin; 5) core height range; and 6) mature leaf green color. This can be seen in Table 1, where the characteristics of NUN 06773 LTL are compared to 3SX4901, when grown under the same environmental conditions.

In certain embodiments the plant of the invention has all the physiological and morphological characteristics, except for certain characteristics mentioned, e.g. the characteristic(s) derived from a converted or introduced gene or trait and/or except for the characteristics which differ.

In one embodiment, the invention relates to a Single Locus Converted plant or a mutated plant of NUN 06773 LTL.

Similarity and differences between two different plant lines or varieties can be determined by comparing the number of morphological and/or physiological characteristics (e.g. the characteristics as listed in Table 1 and/or 2 and/or 3) that are the same (i.e. statistically not significantly different) or that are different (i.e. statistically significantly different) between the two plant lines or varieties when grown under the same environmental conditions. A numerical characteristic is considered to be "the same" when the value for a numeric characteristic is not significantly different at the 1% ($p<0.01$) or 5% ($p<0.05$) significance level, using one way Analysis of variance (ANOVA), a standard method known to the skilled person. Non-numerical or "degree" or "type" characteristic are considered "the same" when the values have the same "degree" or "type" on average when scored using USDA and/or UPOV descriptors, when the plants are grown under the same environmental conditions.

"Distinguishing characteristics" or "distinguishing morphological and/or physiological characteristics" refers herein to the characteristics which are distinguishing (i.e. different) between the new variety (NUN 06773 LTL) and other lettuce varieties, such as the REFERENCE VARIETY, when grown under the same environmental conditions. The distinguishing characteristics between NUN 06773 and REFERENCE VARIETY are described elsewhere herein and can be seen in Table 1, Table 2 and/or Table 3. When comparing NUN 06773 with different varieties, the distinguishing characteristics will be different. In one aspect, the distinguishing characteristics may therefore include at least one, two, three or more (or all) of the characteristics listed in Table 1 and/or 2 and/or 3. All numerical distinguishing characteristics are preferably statistically significantly different at $p<0.05$ between NUN 06773 LTL and the other variety, e.g. REFERENCE VARIETY.

Thus, a lettuce plant "comprising the distinguishing characteristics of NUN 06773 LTL (such as a progeny plant) refers herein to a plant which does not differ significantly from NUN 06773 LTL in characteristics 1), 2), 3), 4), 5) and 6) above. Therefore in one aspect a lettuce plant (such as a progeny plant of NUN 06773 LTL) is provided which does not differ significantly from NUN 06773LTL in the distinguishing characteristics 1), 2), 3), 4), 5) and 6) above.

In a further aspect a lettuce plant (such as a progeny plant of NUN 06773 LTL) is encompassed herein which does not differ significantly from NUN 06773LTL in all or in all but one, two, three, four, five or six characteristics listed in Table 1 and/or 2 and/or 3.

The physiological and/or morphological characteristics mentioned above are commonly evaluated at significance levels of 1%, 5% or 10% if they are numerical, or for having an identical degree (or type) if not numerical, when measured under the same environmental conditions. For example, a progeny plant or a Single Locus Converted plant or a mutated plant of NUN 06773 LTL may have one or more (or all) of the essential physiological and/or morphological characteristics of said variety listed in Table 1 and/or 2 and/or 3, as determined at the 5% significance level (i.e. $p<0.05$) when grown under the same environmental conditions.

As used herein, the term "variety", "cultivated lettuce" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

"Plant line" is for example a breeding line which can be used to develop one or more varieties. A breeding line is typically highly homozygous. Progeny obtained by selfing such a plant line has the same phenotype as its parents.

"Inbred variety" refers to an inbred (nearly homozygous) line or seeds thereof. For example, the (nearly homozygous) plant is self-pollinated or the (nearly homozygous) female parent is pollinated with pollen of the same plant line to produce inbred seeds on the female parent.

"Tissue Culture" refers to a composition comprising isolated cells of the same or a different type or a collection of such cells organized into parts of a plant. Tissue culture of various tissues of lettuce and regeneration of plants therefrom is well known and widely published (see, e.g., Teng et al., HortScience. 1992, 27(9): 1030-1032 Teng et al., Hort- Science. 1993, 28(6): 669-1671, Zhang et al., Journal of Genetics and Breeding. 1992, 46(3): 287-290). Similarly, the skilled person is well-aware how to prepare a "cell culture".

"Vegetative propagation", "vegetative reproduction" or "clonal propagation" are used interchangeably herein and mean the method of taking a part of a plant and allowing that plant part to form at least roots. A plant part is, e.g., defined as or obtained from (e.g. by cutting of) a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, hypocotyl, cotyledon, a rootstock, a pistil, an anther, and a flower or a part thereof, etc. When a whole plant is regenerated by vegetative propagation, it is also referred to as a vegetative propagation.

"Regeneration" refers to the development of a plant from cell culture or tissue culture or vegetative propagation.

"Crossing" refers to the mating of two parent plants. The term encompasses "cross-pollination" and "selfing". "Cross-pollination" refers to the fertilization by the union of two gametes from different plants. "Selfing" refers to self-pollination of a plant, i.e., the transfer of pollen from the anther to the stigma of the same plant. Lettuce is an obligate self-pollination species, which means that pollen is shed before stigma emergence, assuring 100% self-fertilization. Therefore, in order to optimize cross-pollination, a method of misting may be used to wash the pollen off prior to fertilization to assure cross-pollination or hybridization.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

"Locus" (plural loci) refers to the specific location of a gene or DNA sequence on a chromosome, where, for example, a gene or genetic marker is found. A locus may confer a specific trait, such as a resistance or tolerance against a pathogen.

"Genotype" refers to the genetic composition of a cell or organism.

"Allele" refers to one or more alternative forms of a gene at a locus. All of these alleles relate to one trait. Different alleles can result in different observable phenotypes of the trait, such as different pigmentation or a different disease resistance pattern. A variation at the genetic level can also result in little or no observable phenotypical variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

The term "traditional breeding techniques" encompasses herein crossing, selfing, selection, doubled haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one lettuce line or variety to another.

"Progeny" as used herein refers to a plant obtained from a plant designated NUN 06773 LTL. A progeny may be obtained by regeneration of cell culture or tissue culture or parts of a plant of said variety or selfing of a plant of said variety or by producing seeds of a plant of said variety by cross-pollination or by self-pollination. In further embodiments, progeny may also encompass plants obtained from crossing of at least one plant of said variety with another lettuce plant of the same or another variety or (breeding) line, or wild lettuce plants, backcrossing, inserting of a locus into a plant or mutation. A progeny can be a first generation progeny, i.e. the progeny is directly derived from, obtained from, obtainable from or derivable from the parent plant by, e.g., traditional breeding methods (selfing and/or cross-pollinating). However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

The terms "gene converted" or "conversion plant" in this context refer to lettuce plants which are developed by backcrossing wherein essentially all of the desired morphological and physiological characteristics of the parent variety or line are recovered, in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a lettuce variety are recovered in addition to the characteristics of the single locus having been transferred into the variety via the backcrossing technique and/or by genetic transformation and/or by mutation.

"Transgene" or "chimeric gene" refers to a genetic locus comprising a DNA sequence which has been introduced into the genome of a lettuce plant by transformation. A plant comprising a transgene stably integrated into its genome is referred to as "transgenic plant".

It is understood that "significant" differences refer to statistically significant differences, when comparing the characteristic between two plant lines or varieties when grown under the same conditions. Preferably at least about 10, 15, 20 or more plants per line or variety are grown under the same conditions (i.e. side by side) and characteristics are measured on at least about 10, 15, 20 or more randomly selected plant or plant parts to obtain averages. Thus, physiological and morphological characteristics or traits are commonly evaluated at a significance level of 1%, 5% or 10%, when measured in plants grown under the same environmental conditions. Alternatively, "significance" or "statistical significance" of differences can be expressed as a p-value. A p-value represents the probability of obtaining a result equal to or more extreme than the result actually observed. ANOVA is a suitable method for determining the value of p (Clewer, A. G., and D. H. Scarisbrick. 2001 contains a comprehensive explanation of the whole comparison process). Thus, physiological and morphological characteristics or traits are commonly evaluated at a significance level of $p<0.05$ or even more preferably $p<0.01$ when measured in plants grown under the same environmental condition.

"Average" refers herein to the arithmetic mean. The term "mean" refers to the arithmetic mean of several measurements. The skilled person understands that the appearance of a plant depends to some extent on the growing conditions of said plant. Thus, the skilled person will know typical growing conditions for a lettuce variety. The mean, if not indicated otherwise within this application, refers to the arithmetic mean of measurements on at least 10 different, randomly selected plants of a variety or line.

DETAILED DESCRIPTION

The present invention relates to a lettuce (*Lactuca sativa*) variety, designated NUN 06773 LTL, which—when compared to its REFERENCE VARIETY 3SX4901—has: 1) average core height; 2) average core diameter; 3) type of mature leaf blistering; 4) type of undulation of the apical margin; 5) core height range; and 6) mature leaf green color, when grown under the same conditions. Also encompassed by the present invention are progeny plants having all, or all but 1, 2, or 3 of the morphological and/physiological characteristics of NUN 06773 LTL and methods of producing plants in accordance with the present invention.

Thus, in one aspect, the invention provides a seed of the variety designated NUN 06773 LTL wherein a representative sample of seeds of said variety was deposited under the Budapest Treaty, with Accession number NCIMB 42769.

In another aspect, the invention provides a plant of variety NUN 06773 LTL, or a head or a leaf or another plant part thereof, including a tissue or cell culture, a representative sample of seed of said variety has been deposited under the Budapest Treaty, with Accession number NCIMB 42769.

A seed of NUN 06773 LTL is obtainable by selfing the variety and harvesting the produced seeds. The resultant seeds of said variety can be grown to produce plants of said variety. In one embodiment a seed or a plurality of seeds of said variety are packaged into containers of any size or type (e.g., bags, cartons, cans, etc.). The seed may be disinfected, primed and/or treated with various compounds, such as seed coatings or crop protection compounds.

It is understood that a tissue or cell culture of NUN 06773 LTL can be obtained from any plant part of said variety. In one embodiment the invention provides a plant regenerated from the tissue or cell culture of NUN 06773 LTL, wherein the regenerated plant is not significantly different from NUN 06773 in all, or all but one, two or three, of the physiological and morphological characteristics (determined at the 5% significance level or evaluated at p<0.05 using ANOVA) when grown under the same conditions, in one aspect the regenerated plant is not significantly different from NUN 06773 in all, or in all but one, two or three, characteristics listed in Table 1 and/or 2 and/or 3. In these cases, similarity or difference of a characteristic is determined by measuring a representative number of plants grown under the same environmental conditions, determining whether type/degree characteristics are the same or different and determining whether numerical characteristics are significantly different (determined at the 5% significance level or evaluated at p<0.05 using ANOVA) or are not significantly different from NUN 06773 LTL.

A plant of NUN 06773 LTL can be produced by seeding directly in the soil (e.g., field) or by germinating the seeds in controlled environment conditions (e.g., greenhouses) and optionally then transplanting the seedlings into the field (see, e.g., Gonai et al., J. of Exp. Bot., 55(394): 111, 2004; Louise Jackson et al, Publication 7215 ISBN 978-1-60107-007-4 and Publication 7216 ISBN 978-1-60107-008-1 and the world wide web at "anrcatalog.ucdavis.edu" search: lettuce for cultivation, harvesting, handling and postharvest methods commonly used). Lettuce may also be grown in tunnels. Moreover, said variety can be grown in hydroponic cultures as described in, e.g., US 2008/0222949, and the skilled person is familiar with various types of hydroponic cultures. Alternatively, seed of said variety may be grown on peat block for use as root ball lettuce. Furthermore, said variety may be combined with 1, 2 or 3 different lettuce varieties to be grown as "composite lettuce" (see, e.g., EP 1 197 137 A1).

In one embodiment a plant of NUN 06773 LTL, or a progeny plant thereof, comprises at least 3, 4, 5 or or all 6 of the following morphological and/or physiological characteristics when grown under the same environmental conditions (i.e. distinguishing characteristics, as indicated on the USDA Objective description of variety—Lettuce (unless indicated otherwise), where numerical characteristics are averages): 1) average core height; 2) average core diameter; 3) type/degree of mature leaf blistering; 4) type/degree of undulation of the apical margin; 5) core height range; and 6) mature leaf green color. In a different embodiment a plant of NUN 06773 LTL, or a progeny plant thereof, comprises all (or all but one, two or three) of the physiological and morphological characteristic of Table 1, and/or Table 2, and/or Table 3. In a further embodiment a plant of NUN 06773 LTL, or a progeny plant thereof, comprises all physiological and morphological characteristic of NUN 06773 LTL when grown under the same environmental conditions.

In another embodiment NUN 06773 LTL has resistance (on a scale of 1 to 9, where 1 is absent and 9 present) to downy mildew (*Bremia lactucae*) isolate Bl:1 to Bl:32 that is 9 (present) (UPOV characteristic no. 39), resistance to lettuce mosaic virus that is 9 (present) (UPOV characteristic no. 40), resistance to *Nasonovia ribisnigri* that is 9 (present) (UPOV characteristic no. 41).

In still another aspect the invention provides a method of producing a lettuce plant, comprising crossing a plant of lettuce variety NUN 06773 LTL with a second lettuce plant one or more times, and selecting progeny from said crossing.

In yet another aspect the invention provides a method of producing a plant, comprising selfing a plant of variety NUN 06773 LTL one or more times, and selecting a progeny plant from said selfing. In one aspect the progeny plant retains all the distinguishing characteristics of NUN 06773 LTL described above. In a different embodiment the progeny plant comprises all (or all but one, two or three) of the physiological and morphological characteristic of NUN 06773 LTL of Table 1, and/or Table 2, and/or Table 3. In a further embodiment the progeny plant comprises all physiological and morphological characteristic of NUN 06773 LTL when grown under the same environmental conditions.

In other aspects, the invention provides a progeny plant of variety NUN 06773 LTL such as a progeny plant obtained by further breeding that variety. Further breeding with the variety of the invention includes selfing that variety one or more times and/or cross-pollinating that variety with another lettuce plant or variety one or more times. In particular, the invention provides for a progeny plant that retains all the essential morphological and physiological characteristics of NUN 06773 LTL or, in another embodiment, a progeny plant that retains all, or all but one, two or three, of the morphological and physiological characteristics of NUN 06773 LTL, optionally all or all but one, two or three of the characteristics as listed in Table 1 and/or 2 and/or 3, when grown under the same environmental conditions, determined at the 5% significance level for numerical characteristics. In another aspect, the invention provides a vegetative reproduction of the variety and a plant having all, or all but 1, 2, or 3, of the physiological and morphological characteristics of NUN 06773 LTL.

The morphological and/or physiological differences between two different individual plants of the invention (e.g. between NUN 06773 and a progeny of NUN 06773) or between a plant of NUN 06773 LTL or progeny of said variety, or a plant having all, or all but 1, 2, or 3, of the physiological and morphological characteristics of NUN 06773 LTL (or all, or all but 1, 2, or 3 of the characteristics as listed in Table 1 and/or 2 and/or 3) and another known variety can easily be established by growing said variety next to each other or next to the other variety (in the same field, under the same environmental conditions), preferably in several locations which are suitable for said lettuce cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby various characteristics, for example maturity, leaf shape, size and texture, leaf color and glossiness, bolt shape, surface and length, flower size and color, head weight, disease resistance, insect resistance and resistance to physiological stress can be measured and directly compared for species of *Lactuca sativa*.

The morphological and physiological characteristics (and the distinguishing characteristics) of NUN 06773 LTL are provided in the Examples, in Table 1 and/or 2 and/or 3. Encompassed herein is also a plant obtainable from NUN 06773 LTL (e.g. by selfings and/or crossing and/or backcrossing with said variety and/or progeny of said variety) comprising all, or all but one, two or three, of the physiological and morphological characteristics of NUN 06773 LTL listed in Table 1 and/or 2 and/or 3 as determined at the 5% significance level for numerical characteristics or identical for non-numerical characteristics when grown under the same environmental conditions and/or comprising one or more (or all; or all except one, two or three) characteristics when grown under the same environmental conditions.

Also at-harvest and/or post-harvest characteristics of heads or leaves can be compared, such as cold storage holding quality, post-harvest leaf crispness and leaf browning or pinking after cutting can be measured using known methods.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World wide web at rhs.org.uk/Plants/RHS-Publications/RHS-colour-charts).

In a preferred embodiment, the invention provides for a lettuce head or leaf of variety NUN 06773 LTL, or a part of the head or a leaf or a part of a leaf. In another embodiment, the invention provides for a container comprising or consisting of a plurality of harvested lettuce heads or leaves of said variety, or of progeny thereof.

In yet a further embodiment, the invention provides for a method of producing a new lettuce plant. The method comprises crossing a plant of the invention i.e. NUN 06773 LTL, or a plant comprising all but 1, 2, or 3 of the morphological and physiological characteristics of said variety (e.g. as listed in Table 1 and/or 2 and/or 3), or a progeny plant thereof, either as male or as female parent, with a second lettuce plant (or a wild relative of lettuce) one or more times, and/or selfing a lettuce plant according to the invention i.e. NUN 06773 LTL, or a progeny plant thereof, one or more times, and selecting progeny from said crossing and/or selfing. The second lettuce plant may for example be a line or variety of the species *Lactuca sativa*, or other *Lactuca* species or even other *Asteraceae* species.

Progeny includes a later generation (of seeds) produced from the first cross of a lettuce variety of the invention with another plant (F1) or with itself (referred to as F1 or S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g. the F2) with another lettuce plant (and/or with a wild relative of lettuce). Progeny can also refer to a vegetative propagation or a regenerated plant of the invention. Progeny may have all the physiological and morphological characteristics of lettuce variety NUN 06773 LTL when grown under the same environmental conditions and/or progeny may have (be selected for having) one or more of the distinguishing characteristics of lettuce of the invention. Using common breeding methods such as backcrossing or recurrent selection, one or more specific characteristics may be introduced into said variety, to provide or a plant comprising all but 1, 2, or 3 or more of the morphological and physiological characteristics of NUN 06773 LTL (as listed in Table 1 and/or 2 and/or 3).

The invention provides for methods of producing plants which retain all the morphological and physiological characteristics of a plant of the invention i.e. NUN 06773 LTL. The invention provides also for methods of producing a plant comprising all but 1, 2, or 3 or more of the morphological and physiological characteristics of NUN 06773 LTL as listed in Table 1 and/or 2 and/or 3), but which are still genetically closely related to said variety. The relatedness can, for example be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to NUN 06773 LTL if its DNA fingerprint is at least 80%, 90%, 95% or 98% identical to the fingerprint of NUN 06773 LTL. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more.

The invention also provides a plant and a variety obtained or selected by applying these methods on NUN 06773 LTL. Such a plant may be produced by crossing and/or selfing, or alternatively, a plant may simply be identified and selected amongst plants of said variety, or progeny of said variety, e.g. by identifying a variant within NUN 06773 LTL or within progeny of said variety (e.g. produced by selfing) which variant differs from NUN 06773 LTL in one, two or three of the morphological and/or physiological characteristics (e.g. in one, two or three distinguishing characteristics), e.g. those listed in Table 1 and/or 2 and/or 3 or others. For example a variant which produces a different seed color than NUN 06773 LTL can easily be selected in progeny of NUN 06773 LTL. In one embodiment the invention provides a lettuce plant having a Jaccard's Similarity index with NUN 06773 LTL of at least 0.8, e.g. at least 0.85, 0.9, 0.95, 0.98 or even at least 0.99.

The present invention also provides a lettuce seed and a plant produced by a process that comprises crossing a first parent lettuce plant with a second parent lettuce plant, wherein at least one of the first or second parent lettuce plants is a plant provided herein, such as from variety NUN 06773 LTL. In another embodiment of the invention, lettuce seed and plants produced by the process are first filial generation (F1) lettuce seed and plants produced by cross-pollinating a plant in accordance with the invention with another, distinct plant.

The present invention further contemplates plant parts of such an F1 lettuce plant obtained by selfing or cross-pollination, and methods of use thereof. Therefore, certain exemplary embodiments of the invention provide an F1 lettuce plant and seed thereof.

WO2013182646 which is incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed, comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of a plant of the invention i.e. NUN 06773 LTL is a progeny of said variety, because the seed coat of the seed is a maternal tissue genetically identical to NUN 06773 LTL. In one embodiment, the present invention relates to a seed coat comprising maternal tissue of NUN 06773 LTL. In another embodiment the invention relates to a lettuce seed comprising a maternal tissue of NUN 06773 LTL.

By crossing and/or selfing also (one or more) single traits may be introduced into the variety of the invention i.e. NUN 06773 LTL (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g. dominant or recessive) and one or more QTLs (quantitative trait loci) may be transferred into NUN 06773 LTL by breeding with said variety.

Any trait can be introduced. In a preferred embodiment, pest or disease resistance genes may be introduced into a plant according to the invention, i.e. NUN 06773 LTL, progeny of said variety or into a plant comprising all but 1, 2, or 3 or more of the morphological and physiological characteristics of NUN 06773 LTL (e.g. as listed in Table 1 and/or 2 and/or 3). Resistance to one or more of the following diseases or pests is preferably introduced into plants of the invention: Downy mildew, Powdery mildew, *Sclerotinia* rot, *Sclerotinia* drop, *Botrytis* (Grey Mold), *Verticillium* Wilt, *Pseudomonas* spp. (Bacterial Soft Rot), Bacterial Leaf Spot, Anthracnose, Bottom rot, Corky root rot, Lettuce mosaic virus, Turnip mosaic virus, Tomato bushy stunt virus (Dieback), Big vein, Cabbage Loopers, Root Aphid, Green Peach Aphid, Lettuce aphid, Pea leafminer, Beet western yellows and aster yellows. Other resistance genes, against pathogenic viruses (e.g. Lettuce infectious yellows virus (LIYV), lettuce mosaic virus (LMV), Cucumber mosaic virus (CMV), Beet western yellows virus (BWYV), Alfalfa mosaic virus (AMV)), fungi, bacteria or lettuce pests may also be introduced. In one embodiment resistance against *Nasonovia ribisnigri* biotype Nr:0 and/or Nr:1 is introduced a plant of the invention. Other resistance genes, against pathogenic viruses, fungi, bacteria, nematodes, insects or other pests may also be introduced. Also, any resistances to physiological stresses may be introduced into a plant according to the invention, or progeny thereof or into a plant comprising all but 1, 2, or 3 or more of the morphological and physiological characteristics of said plant (e.g. as listed in Table 1 and/or 2 and/or 3. Resistance against one or more of the following is preferably introduced into plants of the invention: Tipburn, Heat, Drought, Cold, Salt and/or Brown rob (Rib discoloration/rib blight).

Thus, the invention also provides a method for developing a plant in a breeding program, using a lettuce plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 06773 LTL or progeny of said variety, or a plant comprising all but 1, 2, or 3 or more of the morphological and physiological characteristics of NUN 06773 LTL (e.g. as listed in Table 1 and/or 2 and/or 3) with a different lettuce plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Brotman et al., Theor Appl Genet (2002) 104:1055-1063). Pedigree selection, also known as the "Vilmorin system of selection," is described in, e.g., Allard, 1960, John Wiley & Sons, Inc.: Principles of plant breeding: 119-128, Library of Congress Catalog Card Number: 60-14240. For breeding methods in general see Principles of Plant Genetics and Breeding, 2007, George Acquaah, Blackwell Publishing, ISBN-13: 978-1-4051-3646-4.

Thus, in one aspect a method for developing a lettuce plant in a lettuce breeding program is provided, using a lettuce plant of the invention, or its parts, as a source of plant breeding material. Suitable plant breeding techniques are recurrent selection, backcrossing, pedigree breeding, line selection, mass selection, mutation breeding and/or genetic marker enhanced selection. For example, in one aspect, the method comprises crossing a lettuce plant designated NUN 06773 LTL, or progeny thereof, or a plant comprising all but 1, 2, or 3 or more of the morphological and physiological characteristics of said plant variety (e.g. as listed in Table 1 and/or 2 and/or 3), with a different lettuce plant selected from the group consisting of a plant of the same variety, a lettuce plant of a different variety, a (breeding) line, or a wild relative of lettuce (e.g., *L. virosa* or *L. serriola*), and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Dziechciarková et al, PLANT SOIL ENVIRON., 50, 2004 (2): 47-58). For breeding methods in general see Principles of Plant Genetics and Breeding, 2007, George Acquaah, Blackwell Publishing, ISBN-13: 978-1-4051-3646-4 or Principles of plant breeding, 1960, Allard, John Wiley & Sons, Inc: Library of Congress Catalog Card Number: 60-14240).

Alternatively, a single trait converted plant or single locus converted plant of NUN 06773 LTL may be produced by the following steps a. obtaining a cell or tissue culture of cells of NUN 06773 LTL;

b. genetically transforming or mutating said cells;

c. growing the cells into a plant; and d. optionally selecting a plant that contains the desired single locus conversion The skilled person is familiar with various techniques for genetically transforming a single locus in a plant cell, or mutating said cells.

In another aspect the invention provides a method of introducing a single locus conversion or introducing a desired trait into a plant designated NUN 06773 LTL, comprising:

(a) crossing the plant designated NUN 06773 LTL, representative seed of which having been deposited under Accession Number NCIMB 42769, with a second plant comprising a desired single locus to produce F1 progeny plants and obtaining progeny of said crossing; wherein the single locus comprised by the second plant is the locus to be introduced in the first plant;

(b) optionally selfing said F1 progeny plant to produce an F2 progeny plant having said single locus;

Said method may be followed by a step of (c) crossing the progeny plant with the plant designated NUN 06773 LTL, representative seed of which having been deposited under Accession Number NCIMB 42769, and obtaining progeny of said cross;

(d) optionally repeating step (c) one or more times in succession to produce selected second or higher backcross progeny plants that comprise the single locus and otherwise comprise essentially all physiological and morphological characteristics when grown under the same environmental conditions of a plant designated NUN 06773 LTL.

The invention is also directed to a lettuce plant obtained from step a), b), c) or d) of the above method.

Any trait can be introduced. In one embodiment the trait to be used in the above method for single locus conversion is disease resistance and the resistance is conferred to any race of *Nasonovia ribisnigri*, any race of Downy mildew, Powdery mildew, *Sclerotinia* rot, *Sclerotinia* drop, *Botrytis* (Grey Mold), *Verticillium* Wilt, *Pseudomonas* spp. (Bacterial Soft Rot), Bacterial Leaf Spot, Anthracnose, Bottom rot, Corky root rot, Lettuce mosaic virus, Turnip mosaic virus, Tomato bushy stunt virus (Dieback), Big vein, Cabbage Loopers, Root Aphid, Green Peach Aphid, Lettuce aphid, Pea leafminer, Beet western yellows and aster yellows, *Sclerotinia minor* (leaf drop), *Sclerotinia sclerotiorum* (leaf drop), *Rhizoctonia solani* (bottom drop), *Erysiphe cichoracearum* (powdery mildew), *Fusarium oxysporum* f. sp. *lactucae* (*Fusarium* wilt), lettuce infectious yellows virus (LIYV), lettuce mosaic virus (LMV), Cucumber mosaic virus (CMV), Beet western yellows virus (BWYV), and Alfalfa mosaic virus (AMV).

The invention also provides a lettuce plant comprising at least a first set of the chromosomes of lettuce variety NUN 06773 LTL, a sample of seed of said variety having been deposited under Accession Number NCIMB 42769; optionally further comprising a single locus conversion or a mutation, wherein said plant has essentially all of the morphological and physiological characteristics of the plant comprising at least a first set of the chromosomes of said variety. In another embodiment, this single locus conversion confers a trait selected from the group consisting of yield, storage properties, color, male sterility, herbicide tolerance, insect resistance, pest resistance, disease resistance, environmental stress tolerance, modified carbohydrate metabolism and modified protein metabolism.

In one embodiment, a plant according to the invention, e.g. NUN 06773 LTL, may also be mutated (by e.g. irradiation, chemical mutagenesis, heat treatment, etc.) and mutated seeds or plants may be selected in order to change one or more characteristics of said variety. Methods such as TILLING may be applied to lettuce populations in order to identify mutants. Similarly, NUN 06773 LTL may be transformed and regenerated, whereby one or more chimeric genes are introduced into the variety. Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 06773 LTL, or progeny of said variety, by transforming said variety or progeny of said variety with a transgene that confers the desired trait, wherein the transformed plant retains all or all but one, two or three of the phenotypic and/or morphological and/or physiological characteristics of NUN 06773 LTL or the progeny of said variety and contains the desired trait.

The invention also provides a plant or a cell of a plant comprising a desired trait produced by mutating a plant of variety NUN 06773 LTL or a cell thereof and selecting a plant the desired trait, wherein the mutated plant retains all, or all but one, of the phenotypic and morphological characteristics of said variety, optionally as described in Table 1 and/or 2 and/or 3, and contains the desired trait and wherein a representative sample of seed of variety NUN 06773 LTL has been deposited under Accession Number NCIMB 42769. In a further embodiment, the desired trait is selected from the group consisting of yield, nutritional value, taste, color, crunchiness, male sterility, herbicide tolerance, insect resistance, pest resistance, disease resistance, environmental stress tolerance, modified carbohydrate metabolism and modified protein metabolism The invention also provides for progeny of lettuce variety NUN 06773 LTL obtained by further breeding with said variety. In one aspect progeny are F1 progeny obtained by crossing said variety with another plant or S1 progeny obtained by selfing said variety. "Further breeding" encompasses traditional breeding (e.g., selfing, crossing, backcrossing), marker assisted breeding, and/or mutation breeding. In one embodiment, the progeny have one or more (or all) of the distinguishing characteristics when grown under the same environmental conditions. In a further embodiment the progeny have all the physiological and morphological characteristics of said variety when grown under the same environmental conditions. In another embodiment the progeny have one, two, or three distinct traits (qualitative or quantitative) introduced into said variety, while retaining all the other physiological and morphological characteristics of said variety when grown under the same environmental conditions.

The invention also provides a plant having one, two or three physiological and/or morphological characteristics which are different from those of NUN 06773 LTL and which otherwise has all the physiological and morphological characteristics of said variety, wherein a representative sample of seed of variety NUN 06773 LTL has been deposited under Accession Number NCIMB 42769. In particular plants which differ from NUN 06773 LTL in none, one, two or three of the characteristics mentioned in Table 1 and/or 2 and/or 3 are encompassed.

In one aspect, the plant having one, two or three physiological and/or morphological characteristics which are different from those of NUN 06773 LTL and which otherwise has all the physiological and morphological characteristics of NUN 06773 LTL differs from NUN 06773 LTL in one of the distinguishing morphological and/or physiological characteristics selected from: 1) average core height; 2) average core diameter; 3) type/degree of mature leaf blistering; 4) type/degree of undulation of the apical margin; 5) core height range; and 6) mature leaf green color.

In another embodiment the plant having one, two or three physiological and/or morphological characteristics which are different from those of NUN 06773 LTL and which otherwise has all the physiological and morphological characteristics of NUN 06773 LTL differs from NUN 06773 LTL in one, two or three morphological or physiological characteristic other than the 6 "distinguishing morphological and/or physiological characteristics" of NUN 06773 LTL: 1) average core height; 2) average core diameter; 3) type/degree of mature leaf blistering; 4) type/degree of undulation of the apical margin; 5) core height range; and 6) mature leaf green color.

A lettuce according to the invention, such as NUN 06773 LTL, or its progeny, or a plant having all physiological and/or morphological characteristics but one, two or three which are different from those of NUN 06773 LTL, can also be reproduced using vegetative reproduction methods. Therefore, the invention provides for a method of producing a plant, or a part thereof, of variety NUN 06773 LTL, comprising vegetative propagation of said variety. Vegetative propagation comprises regenerating a whole plant from a plant part of variety NUN 06773 LTL (or from a progeny of said variety or from or a plant having all physiological and/or morphological characteristics of said variety but one, two or three different characteristics), such as a cutting, a cell culture or a tissue culture.

The invention also concerns methods of vegetatively propagating a plant of the invention. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets.

The invention also provides for a vegetatively propagated plant of variety NUN 06773 LTL (or from progeny of said variety or from or a plant having all but one, two or three physiological and/or morphological characteristics of NUN 06773 LTL), or a part thereof, having one or more distinguishing characteristics and/or all or all but one, two or three of the morphological and physiological characteristics of NUN 06773 LTL when grown under the same environmental conditions.

In one aspect a haploid plant and/or a doubled haploid plant of NUN 06773 LTL, or a plant having all but one, two or three physiological and/or morphological characteristics of NUN 06773 LTL, or progeny of any of these, are encompassed herein. Haploid and doubled haploid (DH) plants can, for example, be produced by cell or tissue culture and chromosome doubling agents and regeneration into a whole plant. For DH production chromosome doubling may be induced using known methods, such as colchicine treatment or the like.

A part of a variety of the invention, i.e. NUN 06773 LTL (or of progeny of said variety or of a plant having all physiological and/or morphological characteristics but one, two or three which are different from those of said variety) encompasses any cells, tissues, organs obtainable from the seedlings or plants, such as but not limited to: a lettuce head or a part thereof, a leaf or a part thereof, a cutting, hypocotyl, cotyledon, seed coat, pollen and the like. Such parts can be stored and/or processed further.

Encompassed are therefore also food or feed products comprising one or more of such parts, such as chopped, sliced, cut, ripped, bagged, preserved, cooked or frozen lettuce heads or leaves from NUN 06773 LTL or from progeny of said variety, such as a plant having all but one, two or three physiological and/or morphological characteristics of NUN 06773 LTL. Such a food or feed product comprises or consists of a plant part described herein wherein the plant part can be identified as a part of the plant of the invention NUN 06773 LTL. Preferably, said plant part is a lettuce head or part thereof or a leaf or a part thereof or an extract from a lettuce head or another plant part described herein.

For example, containers such as cans, boxes, crates, bags, cartons, Modified Atmosphere Packagings, films (e.g. biodegradable films), etc. comprising a plant or a parts of a plant (fresh and/or processed, preferably comprising a head or a leaf) described herein or a seed of NUN 06773 LTL are also provided herein. Marketable lettuce heads or leaves are generally sorted by size and quality after harvest. Alternatively the lettuce heads or leaves can be sorted by leaf size, shape, texture, glossiness or color.

Also provided are plant parts obtainable from variety NUN 06773 LTL (or from progeny of said variety or from a plant having all or all but one, two or three physiological and/or morphological characteristics which are different from those of NUN 06773 LTL or from a vegetatively propagated plant of NUN 06773 LTL (or from its progeny or from a plant having all or all but one, two or three physiological and/or morphological characteristics which are different from those of NUN 06773 LTL), being selected from the group consisting of a head, a harvested head, a part of a head, a leaf, a part of a leaf, pollen, an ovule, a cell, a petiole, a shoot or a part thereof, a stem or a part thereof, a root or a part thereof, a root tip, a cutting, a core, a seed, a part of a seed, seed coat or another maternal tissue which is part of a seed grown on NUN 06773 LTL.

In one embodiment, the invention provides for extracts of a plant described herein and compositions comprising or consisting of such extracts. In a preferred embodiment, the extract consists of or comprises tissue of a plant described herein or is obtained from such tissue.

In still yet another aspect, the invention provides a method of determining the genotype of a plant of the invention comprising the step of detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms.

The method may further comprise storing the results of the step of detecting the plurality of polymorphisms on a computer readable medium.

LIST OF CITED REFERENCES

US 2008/0222949
EP 1 197 137 A1
WO2013182646
Teng et al., HortScience. 1992, 27(9): 1030-1032
Teng et al., HortScience. 1993, 28(6): 669-1671
Zhang et al., Journal of Genetics and Breeding. 1992, 46(3): 287-290
Clewer, A. G., and D. H. Scarisbrick. 2001
Gonai et al., J. of Exp. Bot., 55(394): 111, 2004
Louise Jackson et al, Publication 7215 ISBN 978-1-60107-007-4
Louise Jackson et al, Publication 7216 ISBN 978-1-60107-008-1
Vos et al. 1995, Nucleic Acid Research 23: 4407-4414
Brotman et al., Theor Appl Genet (2002) 104:1055-1063
Allard, 1960, John Wiley & Sons, Inc.: Principles of plant breeding: 119-128, Library of Congress Catalog Card Number: 60-14240
Principles of Plant Genetics and Breeding, 2007, George Acquaah, Blackwell Publishing, ISBN-13: 978-1-4051-3646-4.
Dziechciarková et al, PLANT SOIL ENVIRON., 50, 2004 (2): 47-58). For breeding methods in general see Principles of Plant Genetics and Breeding, 2007

EXAMPLES

Development of NUN 06773 LTL

The inbred variety NUN 06773 LTL was developed from an initial cross between lettuce lines. The female and male parents were crossed to produce seeds. After the cross, progeny were self-pollinated or backcrossed, followed by pedigree selection and line selection. NUN 06773 LTL can be propagated by seeds or vegetatively, or by regeneration of a tissue culture.

The variety is uniform and genetically stable. This has been established through evaluation of horticultural characteristics. Several seed production events resulted in no observable deviation in genetic stability. The Applicant concluded that NUN 06773 LTL is uniform and stable.

Deposit Information

A total of 2500 seeds of variety NUN 06773 LTL were deposited by Nunhems B. V. according to the Budapest Treaty by Nunhems B. V. on May 13, 2017, at the NCIMB Ltd., Ferguson Building, Craibstone Estate, Bucksburn, Aberdeen AB21 9YA, United Kingdom (NCIMB). The deposit has been assigned NCIMB 42769. A deposit of NUN 06773 LTL is also maintained at Nunhems B. V.

Access to the deposits will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The most similar variety to NUN 06773 LTL is herein referred to as REFERENCE VARIETY, and is herein a variety from 3 STAR LETTUCE, LLC., with the commercial name 3SX4901.

In Table 1 and 2 a comparison between NUN 06773 LTL and its REFERENCE VARIETY is shown based on a trial in the USA. Trial location Salinas, Calif., planting date: May 26, 2016, harvesting date: Jul. 25, 2016. In Table 3 additional data on UPOV descriptors based on other trials is collected.

Two replications of 50 plants of each variety, from which 15 plants or plant parts were randomly selected, were used to measure characteristics. For numerical characteristics averages were calculated. For non-numerical characteristics the type/degree was determined. In Table 1 the USDA descriptors of NUN 06773 LTL (this application) and REFERENCE VARIETY (commercial variety) are listed.

In accordance with one aspect of the present invention, there is provided a plant having the physiological and morphological characteristics of NUN 06773 LTL as presented in Table 1 and/or 2 and/or 3.

TABLE 1

Objective description of variety NUN 06773 LTL and its REFERENCE VARIETY.

| USDA descriptor | Application Variety NUN 06773 LTL | Reference Variety 3SX4901 |
|---|---|---|
| Plant type 1 = Cutting/Leaf; 02 = Butterhead; 03 = Bibb; 04 = Cos or Romaine; 05 = Great Lakes Group; 06 = Vanguard Group; 07 = Salinas Group; 08 = Eastern (Ithaca) Group; 09 = Stem; 10 = Latin; 11 = Other (Specify) Seed | 11 (Little Gem) | 11 (Mini Romaine) |
| Color: 1 = White (Silver Gray); 2 = Black (Grey Brown) | n.r. | n.r. |
| Light dormancy: 1 = light required; 2 = light not required | n.r. | n.r. |
| Heat dormancy: 1 = susceptible; 2 = not susceptible Cotyledon to fourth leaf stage | n.r. | n.r. |
| Shape of Cotyledons: 1 = broad, 2 = intermediate, 3 = spatulate | 2 | n.r. |
| Shape of fourth leaf: 1 = Transverse oval; 2 = Round; 3 = oval; 4 = Elongated; 5 = Lanceolate 6 = pinnately lobed | 4 | n.r. |
| LENGTH/WIDTH INDEX OF FOURTH LEAF: LW × 10 | n.r. | n.r. |
| Apical margin: 1 = Entire; 2 = Crenate/Gnawed; 3 = Finely Dentate; 4 = Moderately Dentate; 5 = Coarsely Dentate; 6 = Incised; 7 = Lobed; 8 = Other (Specify) _ | 1 | n.r. |
| Basal margin: (as apical margin) | 1 | n.r. |
| Undulation: 1 = Flat 2 = Slight 3 = Medium 4 = Marked | n.r. | n.r. |
| Green color: 1 = very light green, 2 = light green, 3 = medium green, 4 = dark green; 5 = Very Dark Green; 6 = other | n.r. | n.r. |
| Anthocyanin: Distribution: 1 = absent; 2 = Margin Only (Big Boston); 3 = spotted (California Cream Butter); 4 = throughout (Prize Head); 5 = Other (Specify) | 1 | 1 |
| Anthocyanin: Concentration: 1 = light, 2 = moderate, 3 = intense | n.r. | n.r. |

TABLE 1-continued

Objective description of variety NUN 06773 LTL and its REFERENCE VARIETY.

| USDA descriptor | Application Variety NUN 06773 LTL | Reference Variety 3SX4901 |
|---|---|---|
| CUPPING: 1 = Uncupped 2 = Slight 3 = Markedly | n.r. | n.r. |
| REFLEXING: 1 = None 2 = Apical Margin 3 = Lateral Margins | n.r. | n.r. |
| Mature leaves (harvest mature outer leaves): | | |
| Margin: Incision depth (deepest penetration of the margin): 1 = absent/shallow (Dark Green Boston), 2 = moderate (Vanguard), 3 = deep (Great Lakes 659) | 1 | 1 |
| Margin: Incision density: 3 = sparse, 5 = medium, 7 = dense, 9 = very dense | n.r. | n.r. |
| Margin: Indentation (finest divisions of the margin): 1 = entire, 2 = shallowly dentate (Great Lake 65), 3 = deeply dentate (Great Lake 659); 4 = Crenate (Vanguard); 5 = Other (Specify) | 1 | 1 |
| Margin: Undulations of the apical margin: 1 = absent/slight (Dark Green Boston), 2 = moderate (Vanguard), 3 = strong (Great Lakes 659) | 1 | 2 |
| Green color: 1 = very light green, 2 = light green, 3 = medium green, 4 = dark green; 5 = Very Dark Green; 6 = other | 3 (RHS Green137C) | 4 (RHS Green137B) |
| Anthocyanin: Distribution: 1 = absent; 2 = Margin Only (Big Boston); 3 = spotted (California Cream Butter); 4 = throughout (Prize Head); 5 = Other (Specify) | n.r. | n.r. |
| Anthocyanin: Concentration: 1 = light, 2 = moderate, 3 = intense | n.r. | n.r. |
| Size: 1 = small, 2 = medium, 3 = large | 1 | 1 |
| Glossiness: 1 = dull, 2 = moderate, 3 = glossy | 2 | 2 |
| Blistering: 1 = absent/slight, 2 = moderate, 3 = strong | 2 | 3 |
| Leaf thickness: 1 = thin, 2 = intermediate, 3 = thick | 2 | 2 |
| Trichomes; 1 = absent, 2 = present | 1 | 1 |
| Plant | | |
| Spread of frame leaves (cm) | 23 | 22 |
| Head diameter (market trimmed with single cap leaf) | n.r. | n.r. |
| Head shape: 1 = flattened, 2 = Slightly Flattened; 3 = Spherical; 4 = elongate, 5 = non-heading; 6 = nonheading | 2 | 2 |
| Head size class: 1 = small, 2 = medium, 3 = large | 1 | 1 |
| Head per carton | n.r. | n.r. |
| Head weight (gram) | 281.8 | 288.7 |
| Head firmness: 1 = loose, 2 = Moderate; 3 = Firm, 4 = very firm | 1 | 1 |
| Butt | | |
| Shape: 1 = slightly concave, 2 = flat, 3 = rounded; 4 = V-shaped | 3 | 3 |
| Midrib: 1 = Flattened, 2 = Moderately Raised, 3 = prominently raised | 2 | 2 |
| Core | | |
| Diameter at base of head (mm) | 16.4 | 18.8 |
| Ratio of head spread frame leaves/core diameter | n.r. | n.r. |
| Core height from base of head to apex (mm) | 29 | 34 |
| Range (mm) | 16 to 41 | 24 to 46 |
| Bolting (first water date:) | | |
| Bolting class: 1 = very slow, 2 = slow, 3 = medium, 4 = rapid, 5 = very rapid | n.r. | n.r. |
| Maturity (earliness of harvest-mature head formation) | | |
| Spring (days) | 60 | n.r. |
| Adaptation: Primary regions of adaptation | Adapted to Southwest (CA and/or AZ desert) and West Coast | n.r. |
| Adaptation: Season: 0 = not tested, 1 = not adapted, 2 = adapted | For West Coast, Spring, Summer, Fall, Winter = 2; for Southwest Winter = 2. | n.r. |
| Greenhouse: 0 = not tested, 1 = not adapted, 2 = adapted | 0 | n.r. |
| Soil type: 1 = mineral, 2 = organic, 3 = both | 3 | n.r. |

TABLE 2

| Non USDA descriptor | Application Variety NUN 06773 LTL | Reference Variety 3SX4901 |
|---|---|---|
| Plant Height (cm) at harvest maturity | 12.7 | 16.8 |

TABLE 3

UPOV descriptors of NUN 06673

| UPOV descriptors | NUN 06673 LTL |
|---|---|
| Seed: color 1 white/2 yellow/3 black | 3 |
| Seedling: anthocyanin coloration 1 absent/9 present | 1 |
| Seedling: size of cotyledon (fully developed) 3 small/5 medium/7 large | 3 |
| Seedling: shape of cotyledon 3 narrow elliptic/5 medium elliptic/7 broad elliptic | 5 |
| Plant: type 1 Leaf/2 Mantecosa/3 Bibb/4 Cos or Romain/5 Great Lakes group/6 Vanguard group/7 Imperial group/8 Eastern group/9. Stem/10 American/Latin/11 Other | 11 LITTLE GEM |
| Leaf: attitude at 10-12 leaf stage 1 erect/3 semi-erect/5 prostate | 4 |
| Leaf blade: division 1 entire/2 lobed/3 divided | 1 |
| Plant: diameter 1 very small/3 small/5 medium/7 large/9 very large | 3 |
| Plant: head formation 1 no head/2 open head/3 closed head (overlapped) | 3 |
| Varieties with closed head formation only: Head: degree of overlapping of upper part of leaves 1 very weak/3 weak/5 medium/7 strong/9 very strong | 5 |

TABLE 3-continued

UPOV descriptors of NUN 06673

| UPOV descriptors | NUN 06673 LTL |
|---|---|
| Head: density 1 very loose/3 loose/5 medium/7 dense/9 very dense | 5 |
| Head: size 1 very small/3 small/5 medium/7 large/9 very large | 3 |
| Head: shape in longitudinal section 1 narrow elliptic/2 medium elliptic/3 broad elliptic | 2 |
| Head: shape in longitudinal section 1 Elliptic/2 Broad elliptic/3 Round/4 Transverse elliptic | 2 |
| Leaf: attitude at harvest maturity (outer leaves from head lettuce or adult leaves from cutting and stem lettuce) 1 erect/3 semi-erect/5 horizontal | 4 |
| Leaf Surface roughness: 1 absent or weakly spread/3 weakly spread/5 medium spread/7 strongly spread/9 very strongly spread | 1 |
| Leaf: shape 1 narrow elliptic/2 medium elliptic/3 broad elliptic/4 circular/5 transverse broad elliptic/6 transverse narrow elliptic/7 obovate/8 broad obtrullate/9 triangular | 5 |
| Leaf: shape of tip 1 acute/2 obtuse/3 rounded | 3 |
| Leaf: color of outer leaves: 1 yellowish/2 green/3 greyish-green/4 blueish-green/5 reddish | 2 |
| Leaf: anthocyanin coloration 1 absent/9 present | 1 |
| Leaf blade: degree of undulation of margin 1 absent or very weak/3 weak/5 medium/7 strong/9 very strong | 1 |
| Leaf blade: incisions of margin on apical part 1 absent/9 present | 1 |
| Leaf blade: venation 1 not flabellate/2 flabellate | 1 |
| Axillar sprouting 1 absent or very weak/3 weak/5 medium/7 strong/9 very strong | 1 |
| Time of harvest maturity 1 very early/3 early/5 medium/7 late/9 very late | 5 |
| Time of beginning of bolting under long day conditions 1 very early/3 early/5 medium/7 late/9 very late | 5 |
| Plant: height (at flowering stage) 3 short/5 medium/7 tall | 5 |
| Plant: height (at flowering stage) | 9.9 cm |
| Plant: fasciation (at flowering stage) 1 absent/9 present | 9 |
| Plant: intensity of fasciation (at flowering stage) 1 very weak/3 weak/5 medium/ 7 strong/9 very strong | 3 |

Table 1 and 2 and 3 contain typical values. Values may vary due to environment. Other values that are substantially equivalent are also within the scope of the invention. N.A.=not applicable; n.r.=not recorded.

The invention claimed is:

1. A plant or plant part of lettuce variety NUN 06773LTL, wherein a representative sample of said seed has been deposited under Accession Number NCIMB 42769.

2. The plant part of claim 1, wherein the plant part is a head, a leaf, pollen, an ovule, a fruit, a scion, a rootstock, cutting, flower or a part of any of these or a cell.

3. A seed from which the plant of claim 1 can be grown.

4. A seed grown on the plant of claim 1.

5. A lettuce plant having all of the physiological and morphological characteristics of the plant of claim 1.

6. A seed that produces the plant of claim 5.

7. A tissue or cell culture of regenerable cells of the plant of claim 1.

8. The tissue or cell culture according to claim 7, comprising cells or protoplasts from a plant part selected from the group consisting of embryos, meristems, cotyledons, hypocotyl, pollen, leaves, anthers, roots, root tips, pistil, petiole, flower, fruit, seed, stem and stalks.

9. A lettuce plant regenerated from the tissue or cell culture of claim 7, wherein the plant has all of the physiological and morphological characteristics of the plant of variety NUN 06773 LTL, wherein a representative sample of seed of said variety has been deposited under Accession Number NCIMB 42769, when numerical characteristics are determined at the 5% significance level when grown under the same environmental conditions.

10. A method of producing of the plant of claim 1, or a part thereof, comprising vegetative propagation of NUN 06773 LTL, wherein a representative sample of seed of said variety has been deposited under Accession Number NCIMB 42769.

11. The method of claim 10, wherein said vegetative propagation comprises regenerating a whole plant from a part of NUN 06773 LTL, wherein a representative sample of seed of said variety has been deposited under Accession Number NCIMB 42769.

12. The method of claim 10, wherein said part is a cutting, a cell culture or a tissue culture.

13. A vegetative propagated lettuce plant, or a part thereof, wherein the plant has all of the physiological and morphological characteristics of the plant of claim 1, wherein numerical characteristics are determined at the 5% significance level when grown under the same environmental conditions.

14. A method of producing a lettuce plant, comprising crossing the plant of claim 1 with a second lettuce plant one or more times, and selecting progeny from said crossing and allowing the progeny to form seed.

15. A first generation progeny of the lettuce plant of claim 1 obtained by crossing the plant of lettuce variety NUN 06773 LTL with itself or another lettuce plant.

16. A food or feed product comprising the plant part of claim 2.

17. A lettuce plant grown from the seed of claim 4.

18. A plant of lettuce variety NUN 06773 LTL further comprising a transgene conferring a desired trait and otherwise having all of the morphological and physiological characteristics of the plant of claim 1 when grown under the same environmental conditions, wherein a representative sample of seed of said lettuce variety NUN 06773 LTL is deposited under Accession Number NCIMB 42769, wherein the desired trait is yield, storage properties, color, male sterility, herbicide tolerance, insect resistance, pest resistance, disease resistance, environmental stress tolerance, modified carbohydrate metabolism or modified protein metabolism.

19. A method of producing a modified lettuce plant, the method comprising mutating a lettuce plant or plant part of lettuce variety NUN 06773 LTL, wherein a representative sample of seed of said variety has been deposited under Accession Number NCIMB 42769.

20. The method of claim 19, wherein the desired trait is yield, storage properties, color, male sterility, herbicide tolerance, insect resistance, pest resistance, disease resistance, environmental stress tolerance, modified carbohydrate metabolism or modified protein metabolism.

21. A container comprising the plant or plant part of claim 1.

* * * * *